United States Patent [19]

Braithwaite et al.

[11] 4,400,241

[45] Aug. 23, 1983

[54] EXTRACTIVE DISTILLATION PROCESS FOR THE PRODUCTION OF FUEL GRADE ALCOHOLS

[75] Inventors: David G. Braithwaite; Thomas Cheavens; Jason M. Voyce, all of Tyler, Tex.

[73] Assignee: Improtec, Tyler, Tex.

[21] Appl. No.: 285,307

[22] Filed: Jul. 20, 1981

[51] Int. Cl.³ .................... B01D 3/40; C07C 29/84
[52] U.S. Cl. .................................... 203/18; 203/19; 203/33; 203/56; 203/64; 203/DIG. 13; 44/53; 568/916
[58] Field of Search .............. 203/56, 19, 18, 29, 203/33, DIG. 13, 64, 38; 568/916, 918, 919, 920; 44/77, 53; 426/494, 493

[56] References Cited

U.S. PATENT DOCUMENTS

| | | | |
|---|---|---|---|
| 1,469,447 | 10/1923 | Schneible | 203/19 |
| 1,474,216 | 11/1923 | Van Ruymbeke | 203/19 |
| 1,879,847 | 9/1932 | Gorhan | 203/19 |
| 2,552,412 | 5/1951 | Drout et al. | 203/84 |
| 2,612,468 | 9/1952 | Morrell et al. | 203/53 |
| 3,464,896 | 9/1969 | Washall | 203/18 |
| 3,681,203 | 8/1972 | Ohe | 203/84 |
| 3,989,763 | 11/1976 | Fujii et al. | 568/919 |

*Primary Examiner*—Wilbur L. Bascomb, Jr.
*Attorney, Agent, or Firm*—Llewellyn A. Proctor

[57] ABSTRACT

A novel composition, and extraction process for the dehydration of a hydrated aliphatic, monohydric alcohol to produce a fuel grade alcohol. A select group of alkali-metal and alkaline-earth metal salts are added to and dissolved within a low volatility polyhydric alcohol to form a solution, or solvent extractant, and said solvent extractant contacted and dissolved within said aliphatic, monohydric hydrated alcohol, the solvent extractant distilled, condensed, and a dehydrated fuel grade aliphatic monohydric fuel grade alcohol recovered.

8 Claims, No Drawings

EXTRACTIVE DISTILLATION PROCESS FOR THE PRODUCTION OF FUEL GRADE ALCOHOLS

Considerable attention is being focused on techniques and methods for lowering the costs of producing dehydrated monohydric alcohols, especially those of importance as motor fuels, i.e. the lower molecular weight alcohols such as methyl alcohol, ethyl alcohol, n-propyl alcohol, isopropyl alcohol and the like. The fuel grade alcohols can be used alone in special engines, or in more conventional engines as blends with gasoline, or with gasoline and motor benzole.

Fractional distillation, a conventional method for the recovery of alcohols does not result in the complete removal of water. For example, ethyl alcohol when distilled results in the formation of an azeotrope of the alcohol which contains about five percent water. Whereas solid desiccants, or adsorbents, such as sodium carbonate, potassium chloride, lime, starch and the like can be employed to dehydrate alcohol, the use of such materials burden the process due to the necessity of drying the desiccants for further use. Moreover, even if the non-volatile additives improve selectivity, they often are corrosive, or of limited solubility either in the extractant, or in the alcohol product, causing precipitation in the distillation tower. Absolute ethyl alcohol can also be produced by extractive distillation or azeotropic distillation, but the operation of such processes are costly. Azeotropic distillation, or distillation with the aid of a drying agent such as benzene, diethyl either, or pentane requires added distillation capacity; especially due to the added necessity of recovering the drying agent. Extraction with solvents, with or without distillation, to remove water is also possible. For example, extractive distillation can be carried out with ethylene glycol to dehydrate alcohol. Azeotropic distillation is more sparing of energy than extractive distillation, and hence it is the generally preferred industrial process.

Extractive distillation is thus a long known, but little used process for the production of dehydrated alcohols. The disadvantages of present extractive distillation processes include, inter alia, lack of selectivity which requires large amounts of extractant, and high reflux ratios which increase fuel costs. A detailed comparison of an extractive distillation process wherein ethylene glycol is added to an aqueous ethyl alcohol mixture to produce an overhead separation of ethyl alcohol from water, and an azeotropic distillation process wherein n-pentane is used as an entrainer to separate ethyl alcohol from water, is described by C. Black and D. E. Ditsler in an article entitled "Dehydration of Aqueous Ethanol Mixture by Extractive Distillation" Pages 1–15, *Advances In Chemistry*, Ser. No. 115 (1972). The ethyl alcohol product from the extractive distillation contains 16 ppm water and about 1.2 ppm ethylene glycol for an ethyl alcohol recovery of 99.99 mole %, 46 total equilibrium trays being required with a reflux-feed ratio of 1.55 and a solvent-ethyl alcohol ratio of 4.9 mole basis. The condenser load is about 13.1 million BTU/hour, and the tower is about 4.3 feet based on a Glitch sizing technique. In contrast, in the azeotropic distillation process an ethyl alcohol product containing less water is easily obtained with entrainer-ethyl alcohol ratios of 2.5 to 3.5 mole basis. For a ratio of 3.214, the water content of the alcohol is less than 3 ppm and only 18 trays are required in a column of less than 5 feet diameter. The heat loads in millions BTU/hour are about 10.7 for the reboiler and 11.3 for the condenser. A stripper is used to recover n-pentane and ethyl alcohol from the aqueous phase. Fewer trays are thus required for the azeotropic distillation than for the extractive distillation column, and the heat loads are smaller. Thus, including the stripper for processing the aqueous phase, the total heat load for reboilers for the azeotropic distillation process is less than one-half of that required for the extractive distillation process. The total condenser load is roughly two-thirds of that for the extractive distillation process. The quality of the ethyl alcohol is also slightly better for the azeotropic distillation. Thus, conventional azeotropic distillation processes because of their better selectivity and lesser energy requirements provide profound advantages over conventional extractive distillation processes.

It is, nonetheless, the primary objective of the present invention to provide a novel extraction process which is superior to conventional extraction processes in energy usage.

A specific object is to provide a novel composition, and extraction process which is not only superior to conventional extraction processes, but competitive as well, and even superior to azeotropic distillation processes in that it can provide higher selectivities in removing water from alcohol than azeotropic distillation processes by lowering the amount of extractant needed; as well as lowering reflux ratios which increase fuel cost.

Another object is to provide an extraction process suitable for the efficient recovery of fuel grade alcohols, especially ethyl alcohol, isopropyl alcohol and n-propyl alcohol.

These objects and others are achieved in accordance with the present process which contemplates the use of a select group of alkali-metal and alkaline-earth salts which can be added to, and dissolved within, a low volatility polyhydric alcohol to form a solution, or solvent extractant, and the salt/polyhydric alcohol solvent extractant contacted and dissolved within a hydrated aliphatic monohydric alcohol, and the solvent extractant distilled, condensed, and a dehydrated fuel grade monohydric alcohol recovered. The solvent extractant is more effective in reducing energy usage than azeotropic distillation, vacuum distillation, or the use of adsorbents which lower vapor pressure.

Alkali-metal salts suitable for the practice of this invention are e.g., sodium tetraborate, $Na_2B_4O_7$; potassium phosphate, $K_3PO_4$; potassium bi-phosphate, $K_2HPO_4$, and the like. Alkaline-earth metal salts suitable for the practice of this invention are, e.g., alkaline-earth metal halides such as magnesium chloride, $MgCl_2$; zinc chloride, $ZnCl_2$, and the like. A requirement of these salts is that they are appreciably, if not completely soluble in both the polyhydric alcohol and the alcohol.

A wide variety of polyhydric alcohols, bifunctional hydroxy compounds, or compounds wherein a plurality of the carbon atoms of a chain contain a hydroxyl group, are suitable for the practice of this invention. Suitable compounds are those characterized by the formula $HOCH_2(CHOH)_nCH_2OH$ wherein n is 0 to 5, exemplary of which are tetritols, e.g. erythritol, threitol, D-threitol, L-threitol, D,L-threitol, pentitols, e.g. ribital, arabinitol, D-arabinitol, L-arabinitol, D,L-arabintol, xylitol, hexitols, e.g. allitol, sorbitol, D-mannitol, dulcitol, L-iditol, D-altritol, and heptitols. Other useful polyhydric alcohols are 1,2-propylene glycol, 1,3 propylene glycol, 1,2-, 1,3-, and 2,3-, butylene glycol, 1,2-dihydroxy-3-ethoxy propane, 1,2-dihydroxy-3-methoxy propane, and the like.

The hydrated aliphatic, monohydric alcohol is preferably countercurrently contacted with a low volatility solvent constituted of the polyhydric alcohol and solid absorbent, the solvent being passed downwardly through a still, or column, into contact with an ascending stream of the vaporized hydrated alcohol. Suitably, the low volatility solvent is constituted of from about 80 percent to about 98 percent, preferably from about 85 percent to about 95 percent, of the polyhydric alcohol, and from about 2 percent to about 20 percent, preferably from about 5 percent to about 15 percent of the solid adsorbent, based on the total weight of the polyhydric alcohol and solid adsorbent. Suitably, from about 100 percent to about 800 percent, preferably from about 180 percent to about 500 percent, of the solvent is employed to extract the water from the alcohol, based on the total weight concentration of water contained in said hydrated alcohol. The solvent enhances the volatility of the alcohol more than it enhances the volatility of the water, this permitting the solvent to selectively dissolve and extract the water from the alcohol. Fuel grade alcohol as a vapor is condensed and recovered from the top of the still, or column, and the wet solvent is condensed and passed to a second column for regeneration, or drying, for recovery of the solvent. An additional small column is employed to regenerate the solvent, or extractant, by distilling off the water.

These and other features of the invention will be better understood by reference to the following examples, Examples 1-3 immediately below demonstrating the effectiveness of relatively small amounts of additives for extracting, or removing water from 95% ethyl alcohol (i.e. and admixture of 95 vol % ethyl alcohol and 5 vol % water).

EXAMPLES 1-3

Table 1 below summarizes the results of a series of data obtained by combining 95% ethyl alcohol with a solvent system, or extractant, formed from ethylene glycol or triethylene glycol and a relatively small quantity of $CaCl_2$ or $MgCl_2$, respectively distilled for determination of the composition of the overhead vapor. These results are contrasted with similar runs wherein no salt was added to the ethylene glycol or triethylene glycol. The nature of the additive is given in the first column, the conditions of the distillation are given in the second column, and the initial percent water content is given in the third column of the table.

TABLE I

| Additive | Conditions | Initial % Water Content |
|---|---|---|
| Ethylene Glycol | 8% Distilled | 2.20 |
| Ethylene Glycol + 10% $CaCl_2$ | 8% Distilled | 1.35 |
| Triethylene Glycol | 8% Distilled | 2.90 |
| Triethylene Glycol + 3% $MgCl_2$ | 8% Distilled | 1.35 |
| Ethylene Glycol + 11% $MgCl_2$ | 8% Distilled | 1.30 |

EXAMPLES 4-6

The series of data given in Table II further illustrates the utility of selected solvent additive combinations for enhancing the relative volatility of ethyl alcohol relative to the ethyl alcohol-water system over a range of ethyl alcohol water ratios. An approximately equal weight of (solvent plus additive) and (alcohol plus water) was used in the demonstrations.

TABLE II

| Mole Fraction Alcohol in Alcohol-Water | Solvent | Additive | Relative Volatility |
|---|---|---|---|
| 0.2 | none | none | 6.0 |
| " | glycol | none | 6.3 |
| " | " | $CaCl_2$ | 7.5 |
| " | " | $Na_2B_4O_7$ | 7.3 |
| " | glycerol | none | 6.0 |
| " | " | $CaCl_2$ | 9.5 |
| " | " | $K_2HPO_4$ | 7.8 |
| 0.5 | none | none | 2.3 |
| " | glycol | none | 2.9 |
| " | " | $CaCl_2$ | 3.7 |
| " | " | $Na_2B_4O_7$ | 4.1 |
| " | glycerol | none | 4.0 |
| " | " | $CaCl_2$ | 5.3 |
| " | " | $K_2HPO_4$ | 4.3 |
| 0.8 | none | none | 1.2 |
| " | glycol | none | 1.8 |
| " | " | $CaCl_2$ | 2.3 |
| " | " | $Na_2B_4O_7$ | 3.2 |
| " | glycerol | none | 3.0 |
| " | " | $CaCl_2$ | 4.0 |
| " | " | $K_2HPO_4$ | 3.5 |

The evidence suggests that when an alkali-metal tetraborate, e.g. sodium tetraborate is disolved in glycols and dehydrated by distilling off water, an anionic complex forms between two moles of glycol and one of borate. The structure is formulated as follows:

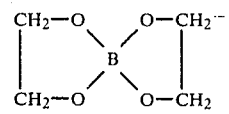

In this case, the associated cation is one-half sodium and one-half hydrogen. With boric acid the cation is hydrogen. The preferred composition is prepared by adding two moles of an alkali-metal hydroxide, e.g. sodium hydroxide, per mole of alkali-metal tetraborate, e.g. sodium tetraborate. The resulting salt is much more soluble than the hydrogen or sodium-hydrogen forms and is not described in the literature. The potassium salt can also be formed from potassium orthoborate ($KBO_2$) or from boric acid and potassium hydroxide, and the lithium salts in a similar manner. The high solubility of these compounds is entirely unexpected.

EXAMPLE 7

Table III summarizes a further series of data, similar to that given in Table II, except that the alcohol is isopropyl alcohol and the only solvent system employed is ethylene glycol containing varying amounts of sodium tetraborate. Again, it is apparent that the additive system of this invention is quite effective in increasing the relative volatility of the alcohol relative to isopropyl alcohol-water mixture.

TABLE III

| Mole Fraction Isopropyl Alcohol | Relative Volatility | |
|---|---|---|
| | No Solvent | Ethylene Glycol + $Na_2B_4O_7$ |
| .98 | .73 | — |
| .97 | — | 2.66 |
| .67 | 1.10 | — |
| .48 | 1.65 | — |
| .45 | — | 3.69 |
| .34 | 2.19 | — |
| .29 | — | 4.49 |
| .25 | 3.55 | — |

TABLE III-continued

| Mole Fraction | Relative Volatility | |
|---|---|---|
| Isopropyl Alcohol | No Solvent | Ethylene Glycol + Na$_2$B$_4$O$_7$ |
| .24 | — | 5.33 |
| .20 | — | 6.15 |
| .17 | 5.51 | — |

Sodium tetraborate and dipotassium phosphate, respectively, in a polyhydric alcohol carrier, or solvent, have been found to provide highly selective extractive solvents for the separation of water from hydrated alcohols. Both of these compounds are non corrosive, and highly soluble in both the alcohol products and carrier polyhydric alcohols.

EXAMPLES 8 AND 9

To illustrate the effectiveness of two particularly preferred extractant solvents, i.e. sodium tetraborate in ethylene glycol, and dispotassium phosphate in glycerol, a determination of the relative volatility of ethyl alcohol vis-a-vis water was made in the presence of the solvent alone and with these additives, with the results being given in Table IV. The large enhancements in relative volatility are evident.

TABLE IV

| Mole Fraction | | Relative Volatility | | |
|---|---|---|---|---|
| Ethanol | Ethylene Glycol | Ethylene Glycol + NA$_2$B$_4$O$_7$ | Glycerol | Glycerol + K$_2$HPO$_4$ |
| 1.0 | 0.5 | 2.0 | 2.8 | 3.7 |
| 0.8 | 1.8 | 2.3 | 3.0 | 4.0 |
| 0.6 | 2.4 | 3.0 | 3.5 | 4.7 |
| 0.4 | 3.6 | 4.6 | 4.5 | 6.2 |
| 0.2 | 6.3 | 7.5 | 5.8 | 9.5 |
| 0.0 | 10.0 | 12.0 | 7.4 | 14.0 |

EXAMPLES 10 AND 11

Using a simplified calculation procedure reported in the October 20, 1980 publication of the *Oil and Gas Journal*, at Pages 138–140, "Shortcut Distillation Program Aids Design" by Henry Y. Mak of Texaco Canada, Ltd., herewith incorporated by reference, the values given in Table IV were used to estimate the design requirements and performance characteristics for a continuous distillation column converting 85% (molar) ethyl alcohol to 99.2% (molar) fuel grade ethyl alcohol. With reference to the results given in Tables V and VI, it will be evident that the reductions in reflux rates produce significant savings in energy cost while equipment costs are reduced by the reduction in the number of required trays.

TABLE V

| | Ethylene Glycol | Ethylene Glycol + Na$_2$B$_4$O$_7$ |
|---|---|---|
| Feed Ethanol (Mole %) | 85.0 | 85.0 |
| Product Ethanol (Mole %) | 99.2 | 99.2 |
| Solvent Ratio | 1.0 | 1.0 |
| Reflux Ratio | 1.2 | 0.4 |
| Theoretical Trays | 38 | 24 |

TABLE VI

| | Glycerol | Glycerol + K$_2$HPO$_4$ |
|---|---|---|
| Feed Ethanol (Mole %) | 85.0 | 85.0 |
| Product Ethanol (Mole %) | 99.2 | 99.2 |
| Solvent Ratio | 1.0 | 1.0 |
| Reflux Ratio | 0.3 | 0.2 |
| Theoretical Trays | 23 | 20 |

EXAMPLE 12

These extractant solvents are also effective for the removal of water from alcohols other than ethyl alcohol. The data given in Table VII illustrates the effectiveness of sodium tetraborate in ethylene glycol for the extraction of water from isopropyl alcohol.

TABLE VII

| Mole Fraction | Relative Volatility | |
|---|---|---|
| Isopropyl Alcohol | No Solvent | Ethylene Glycol + Na$_2$B$_4$O$_7$ |
| .98 | .73 | — |
| .97 | — | 2.66 |
| .67 | 1.10 | — |
| .48 | 1.65 | — |
| .45 | — | 3.69 |
| .34 | 2.19 | — |
| .29 | — | 4.49 |
| .25 | 3.55 | — |
| .24 | — | 5.33 |
| .20 | — | 6.15 |
| .17 | 5.51 | — |

The extractive distillation process of this invention provides a highly energy efficient system, even higher energy efficiency than conventional azeotropic distillation systems; and it presents fewer operational problems. For example, steam usage in distilling hydrated ethyl alcohol to product fuel grade ethyl alcohol can be reduced by approximately 45% as contrasted with a conventional azeotropic distillation process. Thus, a well designed azeotropic distillation system incorporating extensive heat exchange requires 26,000 BTU per gallon of fuel grade ethyl alcohol product whereas, in contrast, the extractive process of this invention requires 13,500 BTU per gallon of fuel grade ethyl alcohol product. The solvents used in the process of this invention, in contrast to those used in azeotropic distillations, e.g. benzene, are relatively non-toxic, non-volatile, less corrosive and have higher flash points.

It is apparent that various modifications and changes can be made without departing the spirit and scope of the invention.

Having described the invention, what is claimed is:

1. An extraction process for the dehydration of a hydrated aliphatic, monohydric alcohol to produce a fuel grade alcohol which comprises forming a solvent extractant by dissolving within a low volatility polyhydric alcohol an alkali-metal or alkaline-earth metal salt selected from the group consisting of sodium tetraborate, potassium orthoborate, potassium phosphate, potassium biphosphate, dipotassium phosphate, and a complex salt prepared by adding two moles of an alkali-metal hydroxide to a mole of an alkali-metal tetraborate, said solvent extractant being constituted of from about 2 percent to about 20 percent of said alkali-metal or alkaline-earth metal salt, and from about 80 percent to about 98 percent of said polyhydric alcohol, based on the weight of the total solvent, contacting and dissolving said solvent extractant within said hydrated aliphatic monohydric alcohol, distilling said solution of solvent extractant and hydrated aliphatic monohydric alcohol, from about 100 percent to about 800 percent of the extractant solvent being employed to extract and dehydrate said monohydric alcohol, based on the total weight concentration of water contained in said monohydric alcohol, and condensing and recovering a dehydrated fuel grade aliphatic, monohydric alcohol from said solution.

2. The process of claim 1 wherein the hydrated aliphatic, monohydric alcohol is countercurrently contacted by said extractant solvent in a distillation column.

3. The process of claim 1 wherein the hydrated aliphatic, monohydric alcohol is passed upwardly through a distillation column and countercurrently contacted by a descending stream of said extractant solvent.

4. The process of claim 1 wherein the solvent extractant is constituted of from about 5 percent to about 15 percent of the alkali-metal or alkaline-earth metal salt.

5. The process of claim 3 wherein the solvent extractant is constituted of from about 5 percent to about 15 percent of the alkali-metal or alkaline-earth metal salt.

6. The process of claim 1 wherein the aliphatic, monohydric alcohol is ethyl alcohol, n-propyl alcohol or isopropyl alcohol.

7. The process of claim 1 wherein the low volatility polyhydric alcohol is ethylene glycol and the salt dissolved therein is sodium tetraborate.

8. The process of claim 1 wherein the low volatility polyhydric alcohol is glycerol and the salt dissolved therein is dipotassium phosphate.

* * * * *